United States Patent [19]

Berti et al.

[11] Patent Number: 5,505,869
[45] Date of Patent: Apr. 9, 1996

[54] LOW SMOKE LUBRICATING COMPOSITION FOR TWO-PHASE ENGINES

[75] Inventors: Franco Berti; Franco Rivetti; Ugo Romano; Umberto Sgambato, all of Milan, Italy

[73] Assignees: Euron S.p.A., Milan; Enichem Synthesis S.p.A., Palermo, both of Italy

[21] Appl. No.: 276,635

[22] Filed: Jul. 18, 1994

[30] Foreign Application Priority Data

Jul. 29, 1993 [IT] Italy ................... MI93A1701

[51] Int. Cl.$^6$ .............................. C10M 105/48
[52] U.S. Cl. .......................... 252/52 A; 252/56 R
[58] Field of Search ................. 252/52 A, 56 R

[56] References Cited

U.S. PATENT DOCUMENTS

| | | | |
|---|---|---|---|
| 2,758,975 | 8/1956 | Cottle et al. | 252/49.8 |
| 2,844,448 | 7/1958 | Heisler et al. | 44/320 |
| 5,114,605 | 5/1992 | Mizui et al. | 252/52 A |
| 5,185,103 | 2/1993 | Eswarakrishnan et al. | 252/606 |
| 5,326,486 | 7/1994 | Mizui et al. | 252/46.6 |

FOREIGN PATENT DOCUMENTS 452816 10/1991 European Pat. Off. .
2321477 3/1977 France .

*Primary Examiner*—Jacqueline V. Howard
*Attorney, Agent, or Firm*—Oblon, Spivak, McClelland, Maier & Neustadt

[57] ABSTRACT

A carbonate ester of an aliphatic triol or tetraol which can be defined with the following formula:

$$R^2-C(CH_2-O-(R'-O)_p-C(=O)-O-R^1)_3 \qquad (1)$$

wherein $R_1$, $R_2$, $R'$ and $p$ are as defined in the description, is used as a lubricating base with a low quantity of smoke for two-phase engines with internal combustion.

Lubricating compositions are described which contain a carbonate ester (1) together with one or more products selected from solvents, bright stock, or other anti-seizing additives, plus normal additives.

9 Claims, No Drawings

LOW SMOKE LUBRICATING COMPOSITION FOR TWO-PHASE ENGINES

The present invention relates to the use of a particular carbonate ester as a lubricating base with a low quantity of smoke for two-phase engines with internal combustion, and compositions which contain said carbonate ester.

Two-phase engines are widely used in the field of two-wheeled vehicles such as motorcycles and scooters, in the field of outboard motors and for agricultural and gardening equipment. In these engines the lubricant is mixed with the fuel and with this enters the combustion chamber where it lubricates the walls of the cylinder and is then burnt together with the fuel. The main technical problems connected to the lubrication of two-phase engines are therefore related to obtaining correct lubrication minimizing the formation of deposits and smokes at the exhaust. The problem of smokes at the exhaust has been particularly and increasingly in the recent past, together with the necessity of using compositions based on biodegradable oils.

The majority of lubricating compositions used in the art for two-phase engines consists of a mineral oil base, a bright stock (mixtures of high viscosity, refined and waxless lubricating oils), additives and, in the case of engines with separate lubrication, also a light hydrocarbon used as diluent to facilitate miscibility in the fuel. More recently the use of a polyisobutene with a high molecular weight has been introduced, to substitute the bright stock, which has reduced the amount of smokes at the exhaust and carbon residues in the engine, without however reaching completely satisfactory results. In addition polyisobutene, like mineral oils, is not biodegradable.

The problem of smoke and biodegradability is particularly felt in the use of agricultural and gardening equipment, where the operator is often very near the exhaust pipe (for example foresters who use motor saws) and where the spreading of oil can be harmful to the working environment and, for the same reasons, in the field of outboard motors.

The Applicants have studied the problem in great depth and have found that the objectives of a limited amount of smoke and biodegradability can be reached by using, in these lubricating compositions, synthetic bases consisting of carbonate esters having a particular structure.

It should be noted that various esters of carbonic acid are used in lubricating and plasticizing compositions in different areas of the art. For example U.S. Pat. No. 2,758,975 describes the use of esters of carbonic acid as bases for lubricants. Chemical Abstracts 71, 1969, 5228f, describes a group of carbonic esters having particular thermal stability, used as lubricants and functional fluids for high temperatures. U.S. Pat. No. 2,739,127 describes the use of organic carbonates as bases for lubricating greases, especially for low temperatures. The U.S. patent describes the use of carbonic esters as bases for lubricating compositions with an improved resistance to extreme pressures. U.S. Pat. No. 2,651,657 describes the use of carbonic esters for lubricants with a low slip point and high viscosity index. German patent 1,006.565 describes the use of carbonic esters as bases for lubricants with improved characteristics, especially at high and low temperatures and with high detergent qualities in the cylinders. Belgian patent 764.900 describes the use of carbonic esters as lubricants and hydraulic liquids, for the lubrication of gears and textile machines and in the processing of metals, with advantages deriving from the high reduction of the friction coefficient and easy biodegradability. European patent application publication No. 89.709 describes the use of carbonic esters as synthetic bases for lubricants having an improved thermal, hydrolytic and oxidative stability. European patent application publication No. 393.749 describes the use of carbonic esters in lubricating fluids for the cold rolling of steel. European patent application publication No. 482.693 describes the use of carbonic esters in lubricating compositions for four-phase, gasoline and diesel engines, for motor vehicles. European patent applications publications No. 421.298 and 426.152 describe the use of carbonic esters in lubricating compositions particularly for refrigerating systems using Freon R-134a, characterized by excellent lubricating and detergent characteristics and mutual solubility with Freon 134a. Chemical Abstracts 116, 1992, 63269d, describes the use of carbonic esters as synthetic lubricants for refrigerating systems. European patent application publication No. 452.816 describes the use of carbonic esters as components of lubricants for refrigerating systems.

These documents of the known art do not indicate any possibility of reducing the amount of smokes at the exhaust of two-phase engines which use particular carbonate esters described hereafter.

Actually attempts have previously been made to solve the problem of reducing the smoke by adding special additives to the oil-fuel mixtures used in two-phase engines. These additives for example can consist of amine or amide salts of a derivative of benzoic or thiobenzoic acid, amine salts of a derivative of phosphoric acid or various hydroxides of quaternary ammonium, as described for example in international patent application WO 92/12224.

As previously specified the present invention is basically based on the discovery that particular carbonate esters of aliphatic triols or tetraols, used as lubricants mixed with a normal fuel for engines with interal two-phase combustion, are capable of substantially reducing the amount of smoke at the exhaust.

In accordance with this, the present invention relates to a carbonate ester selected from those which can be defined with the following formula:

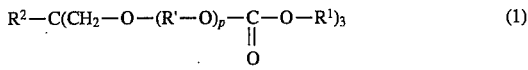
$$R^2-C(CH_2-O-(R'-O)_p-\underset{\underset{O}{\|}}{C}-O-R^1)_3 \qquad (1)$$

wherein:

$R^1$ is an alkyl group, linear or branched, containing from 1 to 20 carbon atoms, $R^2$ is the hydrogen atom, an alkyl group, linear or branched containing from 1 to 20 carbon atoms, or the group:

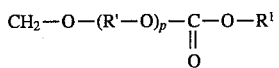
$$CH_2-O-(R'-O)_p-\underset{\underset{O}{\|}}{C}-O-R^1$$

R' is the ethylene group $-(CH_2)_2$ or propylene group $-CH_2-CH(CH_3)$, p is a number varying from 0 to 10;

depending on its use as a lubricating base with a low quantity of smoke, for two-phase engines with internal combustion.

The carbonate esters (I) which can be use according to the present invention are viscous liquids, with a viscosity at 100° C. of from 5 to 50 cSt, and specific examples are:

tetrakis(butylcarbonate) of pentaerythritol, and tris(2-ethylhexylcarbonate) of trimethylolpropane.

The carbonate esters (I) can be prepared starting from alkyl carbonates and polyols, operating under transesterification conditions, in the presence of a transesterification catalyst. Examples of suitable alkyl carbonates are dimethylcarbonate, diethylcarbonate, dibutylcarbonate and di-2-ethylhexylcarbonate. Examples of suitable polyols are trimethylolpropane and pentaerythrite. Examples of suitable catalysts are sodium hydroxide, sodium methylate, trialkyl aluminates, tetra-alkyl titanates, dialkyl stannates of organic acids, and salts, oxides and alkoxides of tin. In the transesterification reaction a molar ratio between alkyl carbonate and polyol is preferably used of about 5:1 to about 20:1 and the operating temperatures are high, for example from 100° to 250° C. At the end of the reaction the carbonate esters are recovered from the reaction mixture using the conventional and known methods.

The invention also relates to a lubricating composition with a low amount of smoke, for two-phase engines with internal combustion, which contains: (a) the carbonate ester together with one or more of (b) solvent, (c) bright stock, or another anti-gripping agent, and (d) usual additives.

The solvent (b) used in the lubricating composition of the present invention is a light hydrocarbon solvent, basically having the function of favouring miscibility with the fuel.

Component (c) is a bright stock, i.e. a mixture of high viscosity, refined wax-free lubricating oils, or consists of another anti-gripping agent, such as for example polyisobutene with a high molecular weight. Obviously mixtures of the above anti-gripping agents can be used.

The additives (d) normally used include dissolving agents, anti-wear agents, antioxidants, corrosion inhibitors, detergents, lowering agents of freezing point, friction modifiers, etc.

Other additives which can be present are anti-knock agents, anti-lead agents, dyes, agents for improving the octane number, antioxidants, rust preventives, bacteriostatic agents, rubber inhibitors, metal deactivators, de-emulsifying agents, lubricants of the upper part of the cylinder and anti-freezing agents.

The lubricating composition of the present invention may generally contain: (a) from 50 to 95% by weight of carbonate ester (I), (b) from 5 to 20% by weight of solvent, (c) from 0 to 15% by weight of bright stock or another anti-gripping agent, and (d) from 0 to 15% by weight of normal additives. In the preferred embodiment, the lubricating composition will contain: (a) 65–70% by weight of carbonate (I), (b) about 10% by weight of solvent, (c) from 5 to 10% by weight of bright stock or other anti-gripping agent, and (d) from 5 to 15% by weight of normal additives.

The lubricating composition of the present invention can be used in two-phase engines with separate lubrication, where it is injected independently of the fuel, or can be used in two-phase engines where it is injected as a mixture with a fuel.

A further aspect of the present invention therefore relates to a mixture with a low quantity of smoke, for two-phase engines with internal combustion, which contains a fuel and the above lubricating composition.

Fuels suitable for the purpose are usually hydrocarbon fuels from the distillation of petroleum, for example a petrol according to ASTM D-439-73. These fuels can also contain non-hydrocarbon materials such as alcohols, and ethers, as well as fuels deriving from vegetable sources. Petrol is particularly preferred, i.e. a mixture of hydrocarbons having an ASTM boiling point of from 60° C. to the distillation point of 10% up to about 205° C. to the distillation point of 90%.

The lubricant-fuel mixtures of the present invention usually contain from 1 to 5% by weight and generally a quantity of about 2% by weight of the lubricating composition described above.

The experimental examples which follow provide a better illustration of the present invention.

EXAMPLE 1

Preparation of tris(2-ethylhexylcarbonate) of trimethylolpropane 87.2 g (0.65 moles) of trimethylolpropane, 1.859 g (6.5 moles) of bis(2-ethylhexyl)carbonate and 0.5 g of sodium methylate in solution at 30% with methanol are charged into a three liter flask, equipped with a distillation column with 20 perforated plates, cooler, liquid dividing head and collector, electromagnetic stirrer, and connected to a vacuum pump.

The following transesterification conditions are applied:

| | |
|---|---|
| residual pressure | 10–12 torr. |
| temperature at bottom | 157–206° C. |
| temperature at head | 70–79° C. |
| reflux ratio | 1/1 |

262 g of 2-ethylhexanol distillate are collected in 1.5 hours.

The deposit (1.685 g) after treatment with carbon dioxide, is filtered and the excess of bis(2-ethylhexyl) carbonate is evaporated in a fine film glass evaporator at 200° C. temperature of the heating oil and 1 torr. of residual pressure.

In this way, tris(2-ethylhexyl carbonate) of trimethylolpropane is obtained as deposit:

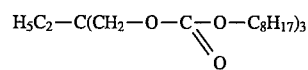

of which 86% in monomeric form, the remaining percentage basically consisting of oligomeric products.

The product thus obtained has the following characteristics:

| | |
|---|---|
| viscosity at 40° C. | 191 cSt |
| viscosity at 100° C. | 14.8 cSt |
| viscosity index | 69 |
| slip point | −30° C. |

EXAMPLE 2

The evaluation of the amount of smoke is carried out on a Yamaha CE50S engine which is first conditioned with a hot functioning cycle at 6,500 rpm and full load for 30 minutes, then cooled for 30 minutes, then heated again at 2,000 rpm with no load for 30 minutes and finally stopped for 30 minutes. 10 accelerations are then carried out under standard conditions during which the opacity of the smoke emitted is measured.

The engine is fed with leadless petrol, with a RON value of 91 and separately with a lubricating composition, in a quantity of from 1 to 5% by weight of the fuel-lubricant mixture, in relation to the number of revs and load.

The following lubricating compostions are specifically tested, the first of which is of the present invention and the others, used for comparative purposes, of the known art:

lubricating composition 1 containing 67% by weight of carbonate ester of example 1, and 33% by weight consisting of additives, anti-gripping agent and solvent;

lubricating composition 2 containing 67% by weight of a commercially available carboxylic ester lubricant, and 33% by weight consisting of additives, anti-gripping agent and solvent, of the same type and in the same quantities as example 1;

lubricating composition 3 containing 67% by weight of another commercially available carboxylic ester lubricant, and 33% by weight consisting of additives, anti-gripping agent and solvent, of the same type and in the same quantities as example 1;

lubricating composition 4 containing 94.7% by weight of Solvent Neutral 150 and 5.3% by weight consisting of identical additives to those of example 1; and lubricating composition 5 containing 94.7% by weight of Solvent Neutral 6000 and 5.3% by weight consisting of identical additives to those of example 1.

The following opacity values of the smoke or were obtained:

| Lubricant composition | Smoke (Abs. %) |
|---|---|
| 1 | 7.8 |
| 2 | 12.4 |
| 3 | 14.1 |
| 4 | 32.1 |
| 5 | 29.8 |

10 tests were made for smoke and the values shown above are the average of the last five tests, the first five being rejected for limited reliability.

EXAMPLE 3

Experiments were carried out on an engine to observe of certain different formulations based on the carbonic ester of example 1. The results were compared to those with parallel formulations based on esters normally available on the market.

The motor-saw engine ALPINA was used according to a test procedure similar to that used by Husqwarna; this consists in running the engine at high power and evaluating, after functioning for 5 hours, the state of the ring zone (ring sticking), the formation of lacquers on the piston (overall piston lacquers), the exhaust port blocking, the formation of deposits in the combustion chamber (total deposit in combustion chamber).

The first series of measurements (table 1) relates to the comparison between formulations which only differ for the type of base used. In table 1, the lubricating composition called CAL-1 consists of 7.5% by weight of polyfunctional additives and 92.5% of the product of example 1. This formulation is compared with two different commercial formulations. The first, called EST-2, consists of 7.5% by weight of the same polyfunctional additives used for CAL-1 and 92.5% by weight of the commercial product consisting of a first ester (called ESTER-2) from carboxylic acid and trimethylolpropane. The second, called EST-1, contains 7.5% by weight of the same polyfunctional additives and 92.5% by weight of a commercial product (called ESTER-1) consisting of a second ester from carboxylic acid and trimethylol propane.

The test in the presence of EST-2 was repeated twice.

TABLE 1

|  |  | CAL-1 | EST-2 | EST-2 | EST-1 |
|---|---|---|---|---|---|
| Piston skirt | 10 min. | 10.0 | 9.8 | 9.23 | 9.37 |
| Land n° 1 | " | 6.16 | 2.07 | 1.14 | 3.78 |
| Ring groove lacquers | " | 7.0 | 1.91 | 0 | 4.23 |
| Undercrown | " | 9.80 | 8.65 | 4.50 | 5.75 |
| Overall piston lacquers | " | 82.4 | 56.1 | 37.2 | 57.8 |
| Exhaust port blocking | " | 10.0 | 9.7 | 9.0 | 10.0 |
| Ring sticking | " | 10 | 3 | 1 | 1 |
| Combustion chamber total deposits (gr.) | " | 0 | 0.05 | 0.07 | 0 |

The data of table 1 show that the formulate containing the product of example 1 allowed the regular functioning of the ring zone up to the end of the test and also gave higher results in terms of the cleanliness of the piston. On the contrary the comparative formulates produced a greater formation of lacquers.

Table 2 shows motoristic data in the presence of formulates also containing solvents.

More specifically CAL-2 is a lubricating composition consisting of 7.5% by weight of the usual polyfunctional additives, 10% by weight of petroleum solvent and 82.5% by weight of the products of example 1.

CAL-3 is a lubricating composition consisting of 8% by weight of the usual polyfunctional additives, 67% by weight of the product of example, 10% by weight of petroleum solvent and 15% by weight of polyisobutene.

The composition EST-3 is shown as a reference (evaluation carried out twice), consisting of 7.5% by weight of the usual polyfunctional additives, 10% by weight of petroleum solvent and 82.5% by weight of a commercial mixture (called ESTER-3) of esters of carboxylic acids and polyols.

TABLE 2

|  |  | CAL-1 | CAL-3 | EST-3 | EST-3 |
|---|---|---|---|---|---|
| Piston skirt | 10 min. | 9.97 | 10.0 | 10.0 | 8.96 |
| Land n° 1 | " | 3.90 | 6.1 | 4.24 | 2.12 |
| Ring groove lacquers | " | 6.28 | 7.55 | 1.56 | 1.25 |
| Undercrown | " | 9.05 | 10.0 | 8.0 | 3.2 |
| Overall piston lacquers | " | 73.0 | 84.1 | 59.5 | 38.8 |
| Exhaust port blocking | " | 9.98 | 10.0 | 10.0 | 9.5 |
| Ring sticking | " | 10.0 | 10.0 | 10.0 | 9.5 |
| Combustion chamber total deposits (gr.) | " | 0.0 | 0.0 | 0.07 | 0.0 |

From table 3 it can be seen that the formulations containing the products of the present invention give excellent results, in particular with respect to the formation of lacquers.

We claim:

1. In a two-cycle internal combustion engine comprising lubricant, the improvement wherein said lubricant comprises a carbonate ester selected from those definable with the following formula:

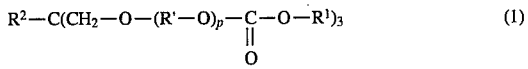

wherein:

$R^1$ is an alkyl group, linear or branched, containing from 1 to 20 carbon atoms, $R^2$ is a hydrogen atom, an alkyl group which is linear or branched containing from 1 to 20 carbon atoms, or the group:

$$CH_2-O-(R'-O)_p-\underset{\underset{O}{\|}}{C}-O-R^1$$

$R'$ is an ethylene group $-(CH_2)_2$ or propylene group $-CH_2-CH(CH_3)$, p is a number varying from 0 to 10.

2. The two-cycle engine according to claim 1, characterized in that the lubricant comprises:

tetrakis(butylcarbonate) of pentaerythritol, or tris(2-ethylhexylcarbonate) of trimethylolpropane.

3. The two-cycle engine as claimed in claim 1, wherein said lubricant further comprises one or more additives selected from dissolving agents, anti-wear agents, antioxidants, corrosion inhibitors, detergents, lowering agents of the freezing point and friction modifiers.

4. The two-cycle engine as claimed in claim 1, wherein said lubricant further comprises one or more of the following: anti-knock agents, anti-lead agents, dyes, agents for improving the octane number, antioxidants, rust preventives, bacteriostatic agents, rubber inhibitors, metal deactivators, de-emulsifying agents, lubricants of the upper part of a cylinder and anti-freezing agents.

5. The two-cycle engine of claim 1, wherein said lubricant comprises (a) from 50 to 95% by weight of said carbonate ester, (b) from 5 to 20% by weight of solvent, (c) from 0 to 15% by weight of bright stock or another anti-gripping agent.

6. The two-cycle engine according to claim 5, characterized in that said lubricant contains (a) 65–70% by weight of said carbonate ester, (b) about 10% by weight of solvent, (c) from 5 to 10% by weight of bright stock or another anti-gripping agent.

7. Fuel-lubricant mixture comprising a fuel and a lubricant, said lubricant comprising a carbonate ester selected from those definable with the following formula:

$$R^2-C(CH_2-O-(R'-O)_p-\underset{\underset{O}{\|}}{C}-O-R^1)_3 \qquad (1)$$

wherein:

$R^1$ is an alkyl group, linear or branched, containing from 1 to 20 carbon atoms, $R^2$ is a hydrogen atom, an alkyl group which is linear or branched containing from 1 to 20 carbon atoms, or the group:

$$CH_2-O-(R'-O)_p-\underset{\underset{O}{\|}}{C}-O-R^1$$

$R'$ is an ethylene group $-(CH_2)_2$ or propylene group $-CH_2-CH(CH_3)$, and p is a number varying from 0 to 10.

8. Fuel-lubricant mixture according to claim 7, characterized in that the fuel is a hydrocarbon fuel from the distillation of petroleum and the lubricant is present in a quantity of from 1 to 5% by weight in the mixture.

9. The two-cycle engine as claimed in claim 1, wherein said lubricant further comprises a solvent.

* * * * *